US00PP37689P2

(12) United States Plant Patent
Tashiro

(10) Patent No.: US PP37,689 P2
(45) Date of Patent: Sep. 8, 2026

(54) ***PETUNIA* PLANT NAMED 'Balslinplant'**

(50) Latin Name: ***Petunia* x *hybrida***
Varietal Denomination: Balslinplant

(71) Applicant: Ball Horticultural Company, West Chicago, IL (US)

(72) Inventor: Rebecca Tashiro, Nipomo, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 19/350,046

(22) Filed: Oct. 5, 2025

(51) Int. Cl.
*A01H 5/02* (2018.01)
*A01H 6/82* (2018.01)

(52) U.S. Cl.
USPC ..... Plt./356.21

(58) Field of Classification Search
USPC ..... Plt./356.1, 356.21
See application file for complete search history.

*Primary Examiner* — Susan Mccormick Ewoldt
(74) *Attorney, Agent, or Firm* — Megan Bowman

(57) ABSTRACT

A new and distinct cultivar of *Petunia* plant named 'Balslinplant', characterized by its pink-purple with purple veined flowers, medium, green-colored foliage, compact- mounded growth habit, is disclosed.

1 Drawing Sheet

Latin name of genus and species of plant claimed: *Petunia* x *hybrida*.

Variety denomination: 'Balslinplant'.

BACKGROUND OF THE INVENTION

The present invention relates to a new and distinct cultivar of *Petunia* plant botanically known as *Petunia* x *hybrida* and hereinafter referred to by the cultivar name 'Balslinplant'.

The new cultivar originated in a controlled breeding program in Arroyo Grande, California during July 2020. The objective of the breeding program was the development of *Petunia* cultivars that have novel flower coloration and have a compact-mounded growth habit.

The new *Petunia* cultivar is the result of cross-pollination. The female (seed) parent of the new cultivar is the proprietary *Petunia* x *hybrida* breeding selection PET-00144-06, not patented, characterized by its light purple flowers, medium, green-colored foliage, vigorous spreading growth habit. The male (pollen) parent of the new cultivar is *Petunia* x *hybrida* 'Ray Purple Vein', not patented, characterized by its medium, purple-colored flowers with dark purple vein pattern, medium, green-colored foliage, and moderately vigorous spreading growth habit. The new cultivar was selected as a single flowering plant within the progeny of the above stated cross-pollination during March 2021 in a controlled environment in Guadalupe, California.

Asexual reproduction of the new cultivar by terminal stem cuttings since March 2021 in Guadalupe, California and West Chicago, Illinois has demonstrated that the new cultivar reproduces true to type with all the characteristics, as herein described, firmly fixed and retained through successive generations of such asexual propagation.

SUMMARY OF THE INVENTION

The following characteristics of the new cultivar have been repeatedly observed and can be used to distinguish 'Balslinplant' as a new and distinct cultivar of *Petunia* plant:

1. Medium pink-purple and purple veined flowers;
2. Medium green-colored foliage;
3. Compact-mounded growth habit.

Plants of the new cultivar differ from plants of the female parent by having darker purple flowers. Plants of the new cultivar differ from plants of the male parent by flowering earlier and having a more vigorous, spreading growth habit.

Of the many commercially available *Petunia* cultivars, the most similar in comparison to the new cultivar is SureShot Pink Vein 'Balsurspinv', not patented. However, in comparison, plants of the new cultivar differ from plants of 'Balsurspinv' in at least the following characteristics:

1. Plants of the new cultivar have flowers with a darker purple coloration than plants of 'Balsurspinv';
2. Plants of the new cultivar have a more vigorous, spreading growth habit than plants of 'Balsurspinv'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Balslinplant'. The approximately 4-month-old plants were grown in 6-inch pots for approximately 13 weeks in a greenhouse in West Chicago, Illinois.

DETAILED BOTANICAL DESCRIPTION

Figure 1:
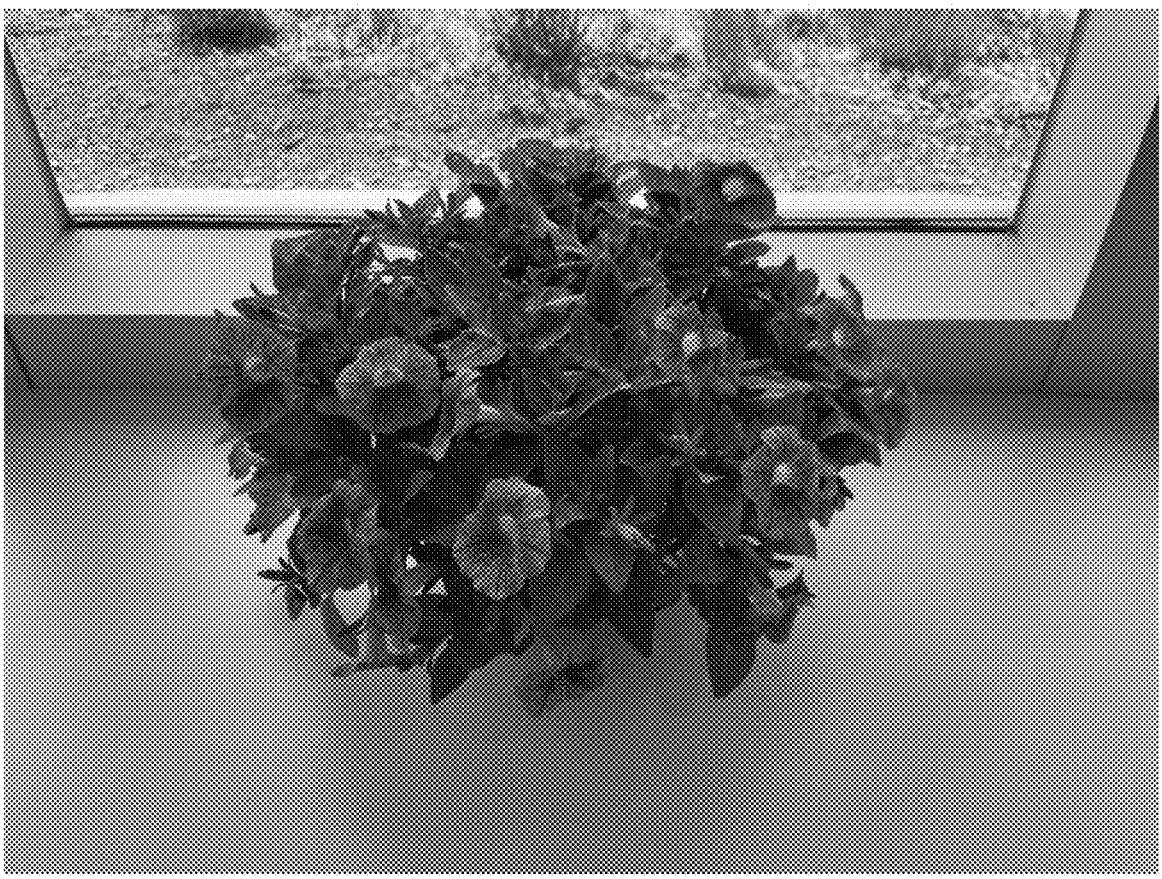
FIG. 1 illustrates a side view of the overall growth and flowering habit of 'Balslinplant'.
Figure 2:
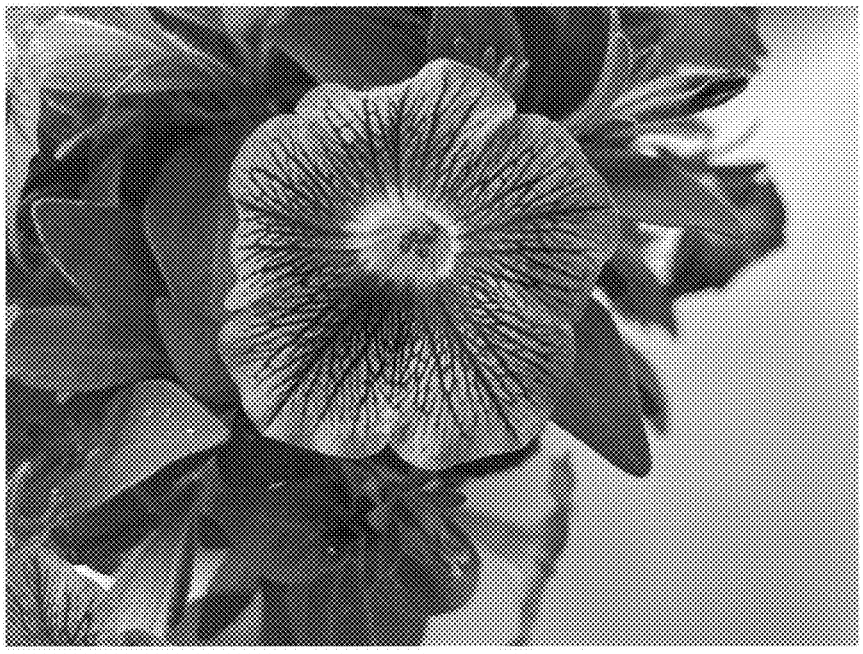
FIG. 2 illustrates a close-up view of an individual flower of 'Balslinplant'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in April 2025 under natural light conditions in West Chicago, Illinois.

The following descriptions and measurements describe approximately 4-month-old plants produced from cuttings from stock plants and grown in a double polyethylene under conditions comparable to those used in commercial practice. The plants were grown in West Chicago, Illinois in 6-inch pots for approximately 4 weeks utilizing a soilless growth medium. Plants were pinched two weeks before transplant. Greenhouse temperatures were maintained at approximately 65° F. to 70° F. (18.3° C. to 21.1° C.) during the day and approximately 60° F. to 65° F. (15.6° C. to 18.3° C.) during the night. Supplemental lighting was used. Measurements and numerical values represent averages of typical plants.

Botanical classification: *Petunia* x *hybrida* 'Balslinplant'.

Parentage:

*Female parent*.—Proprietary *Petunia* x *hybrida* breeding selection PET-00144-06, not patented.

*Male parent*.—*Petunia* x *hybrida* 'Ray Purple Vein', not patented.

Propagation:

*Type cutting*.—Terminal stem.

*Time to initiate roots*.—Approximately 6 to 9 days.

*Time to produce a rooted cutting*.—Approximately 21 to 28 days.

*Root description*.—Fibrous.

*Rooting habit*.—Freely branching.

Plant description:

*Commercial crop time*.—Approximately 5 to 7 weeks from a rooted cutting to finish in a 10 cm pot.

*Growth habit and general appearance*.—Tight, mounded growth habit.

*Size*.—Height from soil level to top of plant plane: Approximately 10.0 cm. Width: Approximately 36.0 cm.

*Branching habit*.—Freely branching. Quantity of main branches per plant: Approximately 5.

*Branch*.—Strength: Moderate. Length: Approximately 13.5 cm. Diameter: Approximately 3.0 mm. Length of central internode: Approximately 1.5 cm. Texture: Densely glandular pubescent. Gland color: Colorless, transparent. Color of young stems: 144C. Color of mature stems: 146A.

Foliage description:

*General description*.—Quantity of leaves per main branch: Approximately 12. Fragrance: Slight. Form: Simple. Arrangement on flowering stem: Alternate.

*Leaves*.—Aspect: Acute angle to stem. Shape: Ovate. Margin: Entire. Apex: Acute. Base: Broadly attenuate. Venation pattern: Pinnate. Length of mature leaf: Approximately 4.5 cm. Width of mature leaf: Approximately 2.5 cm. Texture of upper and lower surfaces: Lightly glandular pubescent. Gland color: Colorless, transparent. Color of upper surface of young and mature foliage: 137B with venation of 146C to indistinguishable. Color of lower surface of young and mature foliage: Closest to 137C with venation of 146D to indistinguishable.

*Petiole*.—Length: Approximately 7.0 mm. Width: Approximately 3.5 mm. Texture: Densely glandular pubescent hairs. Gland color: Colorless, transparent. Color: 143C.

Flowering description:

*Flowering habit*.—'Balslinplant' is freely flowering under outdoor growing conditions with substantially continuous blooming from spring through summer and year-round in greenhouse environment.

*Lastingness of individual flower on the plant*.—Approximately 10 to 12 days.

Flower description:

*General description*.—Type: Simple, salverform. Quantity per plant: Approximately 40. Fragrance: Minimal, sweet.

*Bud*.—Rate of opening: Generally, takes 2 to 3 days for bud to progress from first color to fully open flower. Quantity per plant: Approximately 15.

*Bud just before opening*.—Shape: Oblong. Length: Approximately 3.5 cm. Diameter at apex: Approximately 5.5 mm. Diameter at base: Approximately 2.0 mm. Texture: Densely glandular pubescent. Gland color: Colorless, transparent. Color of petal portion: 77B with venation of 77A. Color of tube: Closest to 145C.

*Corolla*.—Diameter: Approximately 4.5 cm.

*Petals*.—Quantity: 5, fused to form a tube. Shape: Obovate. Appearance: Matte. Margin: Entire, slightly wavy. Apex: Cuspidate to rounded. Length from tube: Approximately 2.3 cm. Length of free portion: Approximately 0.5 cm. Width: Approximately 2.0 cm. Texture of upper surface: Glabrous. Texture of lower surface: Densely glandular pubescent. Gland color: Colorless, transparent. Color of upper surface when first open: 72B to 72C with venation closest to N78A. Color of lower surface when first and fully open: 70B with venation of N81B. Color of upper surface when fully open: NN74D with light venation of 72B.

*Corolla tube*.—Length: Approximately 2.2 cm. Diameter at distal end: Approximately 1.5 cm. Diameter at proximal end: Approximately 2.0 mm. Texture of inner surface: Glabrous. Texture of outer surface: Densely glandular pubescent. Gland color: Colorless, transparent. Color of inner surface: Closest to 145D, venation of 199B. Color of outer surface: Closest to 177D with and overlay and venation of 138A.

*Sepals*.—Quantity per flower: 5, fused at base. Shape: Linear. Margin: Entire. Apex: Acute. Length: Approximately 2.5 cm. Width: Approximately 4.5 mm. Texture of upper and lower surfaces: Densely glandular pubescent. Gland color: Colorless, transparent. Color of upper surface: 137A. Color of lower surface: 138B with 144A at base.

*Peduncle*.—Strength: Strong, flexible. Aspect: Acute angle to stem. Length: Approximately 1.7 cm. Diameter: Approximately 2.0 mm. Texture: Densely glandular pubescent with a mixture of long and short hairs. Gland color: Colorless, transparent. Color: 144B.

*Reproductive organs*.—Androecium: Stamen quantity: 5, basifixed. Stamen length: Approximately 2.0 cm. Filament length of fixed portion: Approximately 7.0 mm. Filament color: NN155C. Anther shape:

Bilobed. Anther length: Approximately 1.0 mm. Anther color: 151D. Pollen amount: Abundant. Pollen color: 189C. Gynoecium: Pistil quantity: 1 per flower. Pistil length: Approximately 1.7 cm. Stigma shape: Funnel. Stigma length: Approximately 1.0 mm. Stigma color: 138A with an overlay of N89. Style length: Approximately 1.6 cm. Style color: 145C. Ovary length: Approximately 3.0 mm. Ovary color: 143A.

Seed and fruit production: Neither seed nor fruit production has been observed.

Disease and pest resistance: Resistance to pathogens and pests common to *Petunia* has not been observed.

What is claimed is:

1. A new and distinct cultivar of *Petunia* plant named 'Balslinplant', substantially as herein illustrated and described.

* * * * *